United States Patent [19]

Quarfoot et al.

[11] Patent Number: 4,909,244
[45] Date of Patent: Mar. 20, 1990

[54] HYDROGEL WOUND DRESSING

[75] Inventors: Alan J. Quarfoot, Palatine; Patrick H. Hyla, Lake Zurich; Donald Patience, Barrington, all of Ill.

[73] Assignee: The Kendall Company, Boston, Mass.

[21] Appl. No.: 935,426

[22] Filed: Nov. 26, 1986

[51] Int. Cl.$^4$ .............................................. A61L 15/00
[52] U.S. Cl. ................................... 128/156; 128/155; 604/304; 424/81; 428/319.3; 428/423.4
[58] Field of Search ................ 128/155, 156; 604/368, 604/897, 892, 894; 106/124, 125, 205; 424/81, 424; 428/319.3, 423.4, 424.2

[56] References Cited

U.S. PATENT DOCUMENTS

| | | | |
|---|---|---|---|
| 446,610 | 2/1891 | Osgood | 128/156 |
| 3,598,122 | 8/1971 | Zaffaroni | 604/897 |
| 4,242,242 | 12/1980 | Allen | 604/368 |
| 4,286,592 | 9/1981 | Chandrasekaren | 128/156 |
| 4,341,207 | 7/1982 | Steer et al. | 128/155 |
| 4,413,621 | 11/1983 | McCracken et al. | 128/155 |
| 4,449,977 | 5/1984 | Korpman | 604/366 |
| 4,538,603 | 9/1985 | Pawelchak et al. | 128/156 |
| 4,601,286 | 7/1986 | Kaufman | 128/155 |
| 4,631,227 | 12/1986 | Nakamura | 128/156 |

OTHER PUBLICATIONS

Alvarez, O. M. et al., "Healing Wounds: Occlusion or Exposure", Infections in Surgery, Mar. 1984, pp. 173-181.

Primary Examiner—Richard J. Apley
Assistant Examiner—Paul Prebilic
Attorney, Agent, or Firm—Alvin Isaacs

[57] ABSTRACT

A wound dressing adapted for preventing pooling of wound exudate and for promoting healing comprises, in order:

(a) a layer consisting essentially of hydrogel for placement on a wound, the hydrogel being characterized as being wound friendly and for absorbing and acting as a reservoir for wound exudate;

(b) an intermediate layer disposed over said hydrogel layer. The intermediate layer comprises a tacky hydrogel or hydrocolloid adhesive, the tacky hydrogel or hydrocolloid adhesive characterized as having a greater absorbent capacity that does the hydrogel in the hydrogel layer; the underlying hydrogel layer is characterized as being more friendly and consequently more suitable for direct wound contact than the overlying adhesive hydrogel of greater absorbent capacity; the intermediate layer having sufficient moisture permeability therethrough to the surface of the dressing;

(c) an outer oxygen- and vapor-permeable layer adapted for transpiration of at least a portion of fluid diffusing through the dressing.

10 Claims, 2 Drawing Sheets

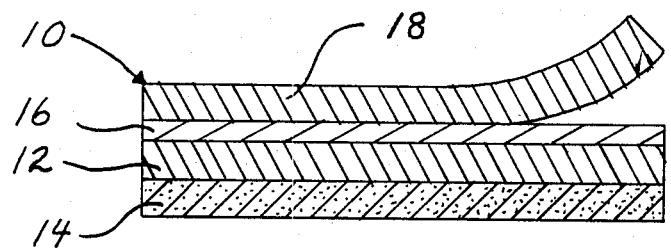
F.G. 1
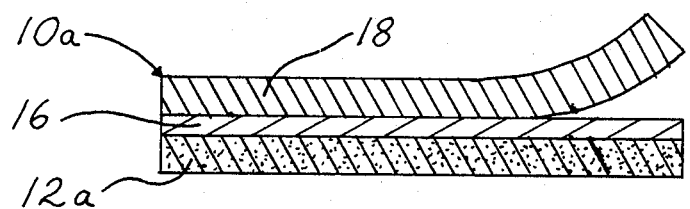
F.G. 2
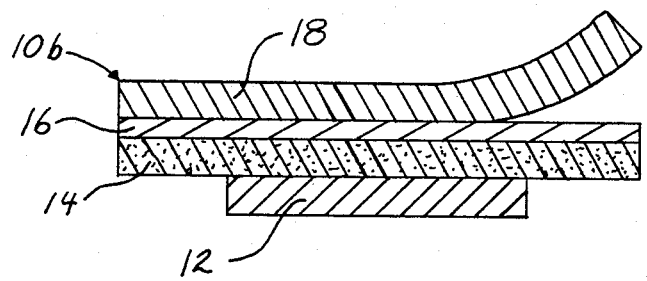
F.G. 3

HYDROGEL WOUND DRESSING

BACKGROUND OF THE INVENTION

In general, dressings to be applied to various types of wounds, including burns and the like, should ideally promote healing, and provide protection, e.g. a bacterial barrier against infection and prevent pooling of wound exudate. While of lesser importance, they should be as comfortable as possible and not cause or contribute to ancillary problems such as bed sores and the like so common with patients bedridden for extended periods of time following surgery or treatment for burns and/or inflicted wounds. Moreover, they should ideally be transparent for visualization and monitoring of the underlying wound.

For convenience, such products will be referred to hereinafter throughout the specification and claims simply as "wound dressings".

Presently, there are essentially only two types of products commercially available for wound dressings, each of which affords certain advantages and, in turn suffers from certain disadvantages.

The first such product is a hydrogel such as "Vigilon" (trademark of C. R. Bard, Inc. for a non-adherent, breathable moist hydrogel which is inert, 96% water and 4% polyethylene oxide.) The Vigilon hydrogel provides a moist environment conducive to wound healing and granulation tissue formation as well as the absorption of wound exudate which would be inherent in the function of hydrogels in general. However, it is not highly absorbent and consequently requires fairly frequent replacement to obviate pooling of exudate and related problems. Moreover, since it is non-adherent to intact skin, it requires the use of adhesive tape for application to the skin as well as gauze or other covering means to prevent escape of the exudate. Apart from the time, trouble and expense of storing and assembling the materials needed to complete the wound dressing, bulky bandages frequently result, particularly where the wound covers a large or irregular surface area. This in turn may contribute to the further discomfort of the patient as well as bed sores from chafing and rubbing. Hydrogels such as Vigilon are disclosed for example, in U.S. Pat. Nos. 3,419,006, 3664,343 and 3,993,551.

For these and perhaps other reasons, a more commonly used product for wound dressings is "Duo-DERM" (trademark of E. R. Squibb & Sons, Inc. for a dressing containing moisture-reactive particles surrounded by an inert, hydrophobic polymer.) The Duo-Derm dressing has ah adhesive inner surface for application to the skin and wound and is said to be virtually impermeable to oxygen. As moisture enter the dressing, the moisture-reactive particles gradually swell, and dissolve to contain the accumulating exudate.

Wound dressings of the DuoDERM structure afford certain advantages, chief of which are the fact that they are unitary structures including the adhesive layer for securing the dressing, ease of application and the ability to contain exudate.

However, they possess certain significant disadvantages, e.g. the adhesive layer is a barrier to diffusion of exudate from the wound so that most of the fluid never diffuses through the adhesive layer; no transpiration of fluid to the atmosphere; the adhesive is aggressive to the intact perilesional skin so that on removal this skin may be traumatized; loss of adhesion in a day or two due to fluid accumulation; tends to exhibit an unpleasant odor when dissolved in wound fluid; and the oxygen-free environment provided by the oxygen- and water-impermeable outer surface provides a favorable environment at the wound locus for the growth of harmful anaerobic bacteria.

The above two products are in Applicant's judgement fairly representative of commercially available wound dressings. Others of course do exist. In addition, the patent literature is replete with references to various types of wound dressings.

While not intending to be a complete survey of the state of the art pertaining thereto, the following patents are nevertheless illustrative.

U.S. Pat. No. 3,249,109 issued to Maeth et al discloses a dressing including a flexible adhesive base composed of hydrated gelatin and including a small amount of pectin, and a fibrous backing member to prevent escape of materials from the base.

U.S. Pat. No. 3,800,792 issued to McKnight et al relates to a surgical dressing particularly useful for the treatment of burn wounds made from a collagen compressed foam film to which has been laminated, without any adhesive, a thin layer of an inert polymer such as polyurethane having a vapor transmission rate slightly higher than that of human skin.

U.S. Pat. No. 4,153,055 issued to Etes relates to a specified semisolid gel adapted for use in contact with the skin. Useful disclosed embodiments include a bandage wherein the gel layer has a fabric backing sheet on one side and a medical adhesive on the other.

U.S. Pat. No. 4,347,841 issued to Benyo et al discloses biological dressings for open wounds. In one embodiment (FIG. 2), the bandage comprises a gel-impregnated fabric having a protective outer layer on one side and a red cell concentrate plus gel former layer on the other side.

U.S. Pat. No. 4,367,732 issued to Poulsen is directed to a skin barrier which may be used for bandaging movable parts of the body, consisting essentially of a non-adhesive, substantially water-impervious elastic film, e.g. polyurethane film, coated with a specified gel-like, at least weakly elastic adhesive composition, the adhesive-coated film being characterized as having a low resistance to quick deformation, and after deformation, a rapid recovery to substantially it original shape.

U.S. Pat. No. 4,516,571 issued to Buchan relates to a device useful for the prophylaxis of pressure sores and which is removably attachable, comprising a mobile moisture-absorbing hydrophilic gel retained within a flexible elastomeric envelope, which envelope has a body contacting surface having a specified vapor transmission rate.

U.S. Pat. No. 4,541,426 issued to Webster disclosed a dressing comprising a conformable apertured film consisting of two layers laminated together, the first being the lesion-contacting layer formed from a material swellable on contact with water, the other either being non-swellable or swells less than the first layer. When in contact with a wet lesion, the different swell characteristics cause the apertures to open to allow passage of water. In the embodiment shown in FIG. 2, a layer of adhesive is provided for adhering to the skin; and in the embodiment of FIG. 3 an absorbent outer layer is present.

U.S. Pat. No. 4,552,138 issued to Hofeditz et al discloses dressings of at least one layer of a specified polymeric, hydrophilic gel, and where relevant, one or more layers of a carrier material as an intermediate and/or covering layer of woven or non-woven fabric or a foam.

Finally U.S. Pat. No. 4,556,056 issued to Fischer et al is directed to a transparent dressing material comprising a dry, swellable clear film of hydrophilic gel in the form of a sheet or strip and which may optionally contain a reinforcing mesh.

As previously stated, a wound dressing should ideally promote healing, provide protection for the wound and prevent pooling of wound exudate.

The present invention has for its task providing a wound dressing which provides all of these important functions and which at the same time is an integral composite structure which is both easy to apply to the wound and also contains all of the components essential for application and retention of the dressing to the skin.

BRIEF DESCRIPTION OF THE INVENTION

In accordance with this invention, the aforementioned task is accomplished by providing wound dressings including at least one hydrogel layer adapted for absorption of exudation from the wound; an adhesive layer for adhering the wound dressing to the skin; and an outer vapor-permeable layer for transpiration of liquid from the dressing. The adhesive for adhering the dressing may be a hydrogel-containing layer itself or it may be a separate layer.

In the preferred embodiments, a non-adhesive hydrogel layer is applied directly to the wound.

BRIEF DESCRIPTION OF THE DRAWINGS

FIGS. 1-6 are diagrammatic, sectional views illustrating alternative embodiments of this invention.

DETAILED DESCRIPTION OF THE INVENTION

Figure 4:
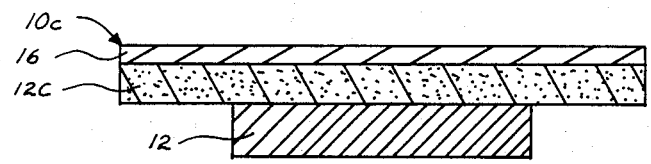

The present invention relates to integral, composite wound dressings employing a hydrogel layer for absorbing and retaining exudate as well as an outer layer which protects the dressing and the wound while at the same time being vapor-permeable to permit transpiration of liquid and thus provide maximal protection against pooling.

The composite dressing also includes an adhesive for securing the dressing in place and thereby provides, in a composite structure, all of the essential elements for the dressing, including adhesion to the skin.

The concept of employing hydrogels for wound dressings is per se known and shown, for example, in certain of the prior art references previously discussed.

As is known, hydrogels in general possess the ability to absorb and retain large quantities of liquid such as wound exudate. By way of illustration, U.S. Pat. No. 4,300,820 issued to Shah relates to a novel class of hydrogels useful for wound dressings, which can absorb more than 45% of their weight of water and may even absorb more than ten times their weight of water, depending upon their composition and ratios of ingredients. Other useful hydrogels include those recited in the aforementioned U.S. Pat. Nos. 3,419,006; 3,664,343 and 3,993,551, as well as others heretofore known in the art.

For a further understanding of the nature and objects of the invention, reference is made to the accompanying illustrative drawings.

As shown in FIG. 1, wound dressing 10 comprises, as essential elements, an oxygen- and water vapor-permeable outer layer 16, hydrogel layer 12 and adhesive layer 14. In the illustrated embodiment, a vapor impermeable removable outer sheet 18 is also provided.

Sheet 18, which may be made of any suitable material such as ethylene vinyl acetate and which may be on the order of 1 to 10 mils thick, serves as a support for the dressing prior to application and further serves as a moisture barrier to prevent drying of the hydrogel during the dressing shelf life. However, it will be appreciated that where the essential components of the dressing possess sufficient dimensional stability, sheet 18 may be eliminated, in which event the requisite moisture barrier during shelf life may be provided by suitable packaging means e.g. a metal foil or plastic wrap.

Oxygen- and vapor-permeable layer 16, which may further serve as a bacterial barrier, is preferably transparent, as is the hydrogel layer, for observing the wound. It is preferably as thin as possible, e.g. on the order of one mil thick, but may be thicker if desired. As examples of useful materials for layer 16, mention may be made of polyurethanes, e.g. "Pellethane" (trademark of Upjohn for a polyether polyurethane) "Pebax" (trademark of ATOCHM, Inc. for a polyether block polyamide) etc.; polymers such as "Hytrel" (trademark of duPont for a copolyether-ester polymer comprising butylene terephthalate segments and polyalkylene ether glycol segments); and the like.

Hydrogel layer 12, which may be any of the per se known hydrogels heretofore employed for wound treatment such as those previously mentioned, maybe on the order of 5-250 mils thick and should most preferably be on the order of 50-150 mils thick. As will be appreciated, it should preferably be selected from those hydrogels known to have the capacity to absorb relatively large amounts of fluid.

Adhesive layer 14 may be an acrylic or rubber pressure-sensitive layer of per se known composition, which layer will typically contain other components or reagents performing specific desired functions, e.g. tackifiers, fillers, bactericides, medicaments or other bioactive agents, etc. Preferably, the adhesive layer should be as thin as possible consistent with its function of adhering the dressing to the skin. It may for example be on the order of 1 to 15 mils thick.

Preferably, a release sheet (not shown), e.g. a per se known silicone release paper, is releasably secured to protect adhesive layer 14 prior to application.

As will be appreciated, for application, the release sheet is removed, the dressing then placed on the wound, and, finally, the removable top sheet 18 is peeled away.

Dressing 10 may be said to constitute the least sophisticated form of the present invention in terms of its structure and may further be said to be the least preferable embodiment in so far as the arrangement of elements is concerned.

As was previously mentioned with respect to the prior art, positioning the adhesive component closest to the wound tends to inhibit diffusion of exudate to the hydrogel layer and subsequent transpiration to the ambient air. Moreover, the adhesive layer would tend not to be "wound friendly" in the sense that it may contribute to wound trauma on removal. However, it is possible to minimize these disadvantages in the described structure.

For example, the adhesive layer may be rendered more permeable to exudate diffusion by rendering it porous. This may be accomplished, for example, by mixing an innocuous chemical blowing agent (CBA)

with the adhesive formulation and then heating to form an adhesive melt. As is known and understood, CBA's will, in general, release nitrogen as the primary gas upon reaching its decomposition temperature along with smaller quantities of a secondary gas or gases, e.g. carbon dioxide. By controlling the temperatures employed, the cell size of the resulting foam may be selected. Foaming or aeration may also be provided by other means known in the art, e.g. direct injection of a gas, volatile liquid or nucleating agent. The resulting porous adhesive melt may then be coated onto the hydrogel layer in known manner, e.g. extrusion coating, calendering, etc. If found desirable or expedient to do so, it will be appreciated that intermediate layers, e.g. tie coats or the like may be disposed between the hydrogel and adhesive layers.

The inherent problem of trauma by adhesive contact may in turn be minimized if not precluded by employing pressure-sensitive adhesives which will at least in part lose their tackiness upon retention in contact with moisture such as wound exudate. Adhesives of this nature are known in the art and consequently per se comprise no part of this invention.

FIG. 2 illustrates an alternate embodiment of the invention. As shown therein, dressing 10a comprises removable impermeable sheet 18, oxygen- and vapor-permeable layer 16 and hydrogel layer 12a which includes a tackifier and/or possesses sufficient surface tack to retain the wound dressing in place. By employing a tacky hydrogel layer 12a, the need for a separate adhesive layer is obviated. This in turn will improve exudate absorbency and subsequent transpiration as well as simplifying manufacture.

As previously mentioned with respect to FIG. 1, support sheet 18 may be eliminated if the wound dressing otherwise possesses sufficient dimensional stability for handling and application to the wound.

FIG. 3 illustrates another embodiment of this invention wherein dressing 10b is illustrated to comprise, in order, removable support 18, oxygen- and vapor-permeable layer 16, adhesive layer 14 and hydrogel layer 12. As seen, hydrogel layer 12, adapted for placement over the wound, is of shorter dimension than adhesive layer 14, thus providing peripheral areas of the adhesive layer extending beyond the hydrogel layer for adherence to the skin surrounding the wound. Preferably, the hydrogel layer is centrally positioned on the adhesive layer and is of sufficiently smaller surface area to provide a margin of at least one inch of adhesive surface beyond the periphery of the hydrogel to insure proper adhesion of the dressing.

Wound dressing 10b affords the further advantage of having the "wound friendly" hydrogel applied directly to the wound, thereby increasing the speed and efficiency of diffusion of exudate from the wound surface over that normally attainable when the exudate must first diffuse through an intermediate adhesive layer.

FIG. 4 illustrates a particularly preferred embodiment of this invention.

As shown, dressing 10c comprises, in order, a permeable layer 16 as previously described, a thin layer 12c of a water-activated hydrogel or hydrocolloid adhesive and a hydrogel layer 12 which, similar to the embodiment shown in FIG. 3, is of smaller surface area than adhesive layer 12c and is preferably centrally positioned and adhered thereto.

Oxygen- and vapor-permeable layer 16 is preferably thin, e.g. on the order of one mil for optimum moisture transpiration. As previously stated, it may comprise a per se known film having these permeability characteristics, e.g. Pellethane, Hytrel or Pebax.

Adhesive layer 12c may also be relatively thin, e.g. on the order of 1-10 mils thick. However, it may, if desired be appreciably thicker, e.g. on the order of 50 mils and such thicker layers may in fact be preferable in some instances. While water-activated hydrogel adhesives are generally preferred, as eluded to above layer 12c may instead comprise a water-activated hydrocolloid adhesive.

As examples of useful hydrogels for layer 12c, mention may be made of those comprising a polymer of 2-acrylamido-2-methylpropane sulfonic acid or a salt thereof which are described , for example in U.S. Pat. Nos. 4,391,278 or 4,242,242, or Canadian Pat. Nos. 1,173,114, 1,173,116 or 1,173,115, all assigned to Medtronic, Inc.; the gels commercially available from Medtronic Inc. under the trademarks "EnerTac" NDO Gel and "EnerTac" HH Gel, etc.

Suitable hydrocolloids for layer 12c include "Hydroactive" (trademark of E.R. Squibb & Sons for the absorbent/adhesive employed in the aforementioned DuoDERM dressing); and the like.

Hydrogel 12 is preferably appreciably thicker than layer 12c and may, for example, be on the order of 50 to 150 mils thick.

In the composite structure of FIG. 4, the thicker "slab" of hydrogel 12 (which may be the same as or different from layer 12c) may be regarded as the primary hydrogel component for absorption of exudate. When the dressing is in place, the thinner layer 12c surrounds "slab" 12, thereby providing the advantage of stabilizing layer 12 in place on the wound. Moreover, outer layer 16 provides a low friction sliding surface which, in turn, materially inhibits accidental catching or snagging of main hydrogel layer 12 which may cause its removal or disturbance of the wound.

A significant advantage of this embodiment of the invention is that it provides an increased area for water vapor transmission than does the exposed surfaces of hydrogel layer 12 alone.

Since the overlapping film or layer of the outer surface of the hydrogel layer is usually the rate limiting component for water vapor transmission or transpiration, in the structure shown in FIG. 4, wound fluids will move from the wound into hydrogel layer 12, through layer 12 to the the layer 12/adhesive 12c interface, and what is not permitted to transpire to the atmosphere will then move laterally in layer 12c to provide even more surface area for evaporation of water.

It should further be noted that as moisture traverses the skin contact area of layer 12c, an additional source of water is thereby provided to enhance the adhesion of water-activated adhesive layer 12c, thus further stabilizing the composite wound dressing in place on the skin.

It will also be appreciated that water vapor escaping the lateral edges of hydrogel slab 12 can be absorbed by layer 12c, thereby providing another path for water movement/transfer. This is a significant advantage when one considers that the rate of water evaporation is important to control at the higher levels in the active secreting stages of wounds in order to lengthen the functional life of the dressing, i.e. to increase the time the dressing may be functionally retained on the wound.

The general composite structure of FIG. 4 may also be utilized to take advantage of the properties of certain types of hydrogels without concurrently having the inherent disadvantages of these hydrogels.

While hydrogels are in general attractive wound dressing materials in the sense that they are "wound friendly", provide a moist environment conducive to wound healing, act as a bacterial barrier, provide mechanical protection for the wound, act as a thermal insulator and, as heretofore noted, absorb large amounts of wound fluids, they generally fall into one of two categories:

(1) those such as the aforementioned "Vigilon" which are only moderately absorbent and exhibit minimal tack; and (2) those such as the aforementioned Medtronic NDO hydrogel and other acrylic based hydrogels which possess inherent tack and good absorptive properties but because of their adherence to the wound tissues can cause trauma when the dressing is changed.

With a composite structure such as illustrated in FIG. 4, the former type which is non-tacky and more conducive to wound healing but possesses low absorbency may be employed as layer 12; and the tacky hydrogel having the greater absorbent capacity but which may not be suitable for direct wound contact is employed as layer 12c.

With such a composite structure it will be seen that, unlike the prior structures, the hydrogel in contact with the skin need not be highly absorbent in order to prevent pooling. Conversely, the hydrogels which possess the requisite absorbent potential but which can cause trauma or are otherwise unsuitable for direct wound contact also need not be applied to the wound.

Employment of the two-component system as described above with the non-adhesive, lesser absorptive hydrogel in contact with the wound and the more absorptive tacky overlying absorbent material retaining the dressing in place will provide an environment which is conducive to healing as well as relief of symptomatic discomfort. Additionally, the adhesive absorbent will hold the dressing in place and act as an additional reservoir for absorption of exudate and subsequent transpiration. As previously discussed, the overlying adhesive absorbent will also absorb fluid which moves laterally across the wound and/or intact skin as well as fluid which moves vertically through the non-adhesive hydrogel covering the wound surface.

Figure 5:
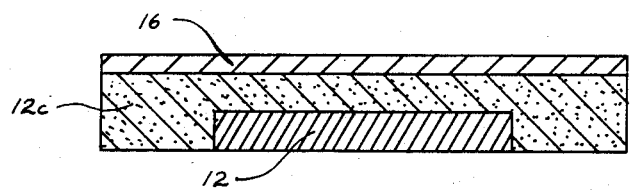

FIG. 5 shows a variation in structure of the embodiments discussed with respect to FIG. 3.

As shown therein, adhesive layer 12c also surrounds the lateral edges of hydrogel layer 12 rather than having layer 12 adhered only to the inner surface of layer 12c.

Figure 6:
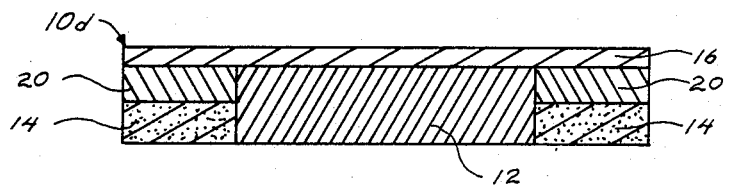

FIG. 6 illustrates yet another embodiment of the present invention. As shown, wound dressing 10d has a oxygen- and moisture permeable film or layer 16 onto which a non-tacky or only slightly tacky hydrogel layer 12 of smaller dimensions is substantially centrally secured. On the free inner surface of film or layer 16 a shape retaining member 20, such as a polyethylene foam is positioned. Shape retaining member 20, which is less thick than hydrogel layer 12, carries a pressure-sensitive adhesive coating 14 on its free inner surface, the combined thickness of member 20 and adhesive coating 14 being shown to be substantially the same as the thickness of hydrogel layer 12.

As is the case with the previous illustrative embodiments, a release sheet is preferably provided on the inner (lower) surface of the dressing to protect the adhesive and hydrogel layers and a removable impermeable sheet may be provided over the outer (top) surface.

As will be apparent, adhesive 14 secures the dressing to the skin surrounding the wound, while hydrogel 12 is positioned directly on the wound The foam or other shape retaining member around the periphery of the dressing provides shape and strength to the dressing and may optionally possess some moisture absorbent properties.

The various embodiments which have been described and are shown in the illustrative drawings are susceptible to various modifications in structure without departing from the invention herein described. Various intermediate layers providing specific desired functions may be employed if found advisable or expedient to do so.

For example, it may be desired to provide a matrix for the controlled delivery of a bioactive agent, e.g. a medicament, to the wound locus. It is also postulated that a woven or non-woven cloth scrim may be provided in a separate layer or, in lieu thereof, it may be incorporated in the hydrogel layer itself in order to provide increased strength and dimensional stability or integrity to the dressing.

The following example shows by way of illustration and not by way of limitation the practice of the present invention.

EXAMPLE

A wound dressing having the preferred structure shown in FIG. 4 was prepared in the manner described hereinbelow.

A sterile layer of "EnerTac" NDO gel approximately 2.5 inches ×2.5 inches was adhered to one surface of a "Pellethane" No. 2363-80AE urethane film which, in this particular example, was slightly larger, measuring about 3 inches ×3 inches. A slab of sterile "Vigilon" hydrogel dressing measuring about 1.5 inches ×1.5 inches was then centrally positioned on the free surface of the NDO adhesive hydrogel, leaving about 0.5 of an inch of adhesive surface around the periphery of the Vigilon layer for adherence to the skin. In accordance with conventional test procedures, a wound approximately 1.5 cm × 1.5 cm was made on a pig. After achieving hemostasis, the wound was covered with the above dressing so that the Vigilon layer completely covered the wound.

By gross observation and histologic results provided by standard protocol it was found that the wound closed rapidly with the reestablishment of normal tissue architecture with minimal inflammation (Grade 1 on a scale of 1 to 4).

Microscopic findings of the formalin fixed, sectioned and stained tissue taken at 29 days post-wounding showed the following:
No scab,
epithelial covering complete,
pigment, macrophages present,
slight congestion, fibrous tissue and inflammatory infiltration,
moderate fibroblast proliferation,
minimal eosinophilic deposits and granulomatous reaction, and
primary cell type: lymphoid In view of the foregoing description and illustrative example it will be seen that the present invention provides a composite structure containing all of the essential components for a wound dressing, the invention further being adapted for providing a wound friendly dressing capable of providing rapid healing results.

Since certain changes may be made without departing from the scope of the invention herein described, it is intended that all matter contained in the foregoing description, including the examples and drawings, shall be taken as illustrative and not in a limiting sense.

We claim:

1. A wound dressing comprising, in order:
an outer oxygen- and vapor-permeable layer;
a shape retaining member secured to peripheral portions of the inner surface of said outer layer extending from the perimeter of said outer layer towards the center thereof;
an adhesive layer adhered to the inner surface of said shape retaining means, said shape-retaining member means and said adhesive layer together defining a well on the inner surface of said outer layer, the dimensions of said well being defined by the width and combined thickness of said shape retaining member and adhesive layer; and
a layer consisting essentially of hydrogel adapted for absorbing wound exudate seated within said well.

2. A dressing as defined in claim 1 wherein said shape retaining member comprises a foam material.

3. A composite wound dressing comprising a layer consisting essentially of hydrogel adapted for absorption of exudation from said wound; an adhesive material for adhering the dressing to the skin surrounding the wound; an outer oxygen- and vapor-permeable layer for permitting transpiration of liquid from said dressing to ambient air; and a removable vapor impermeable sheet material releasably secured on the outer surface of said oxygen- and vapor-permeable layer; said adhesive material being present in a layer between said outer layer and said hydrogel layer, said hydrogel layer having smaller surface dimensions than said adhesive layer, whereby said adhesive layer has free surface areas extending beyond the periphery of said hydrogel layer for adhering said dressing to the skin.

4. A wound dressing as defined in claim 3 wherein said adhesive layer comprises a layer of absorbent adhesive.

5. A wound dressing as defined in claim 4 wherein said absorbent adhesive comprises an adhesive hydrocolloid or hydrogel.

6. A wound dressing as defined in claim 5 wherein said outer layer is transparent.

7. A wound dressing adapted for preventing pooling of wound exudate and for promoting healing comprising, in order:
(a) a layer consisting essentially of hydrogel for placement on a wound, said hydrogel being characterized as being wound friendly and for absorbing and acting as a reservoir for wound exudate, said hydrogel further being characterized as being fluid-permeable whereby said exudate can diffuse, at least in part, through said hydrogel layer toward the outer surface of said dressing;
(b) an intermediate layer disposed over said hydrogel layer and having greater dimension than said hydrogel layer whereby portions of said intermediate layer extend beyond the periphery of said hydrogel layer, said extended portion of said intermediate layer having an adhesive surface for adhering said dressing to the skin, wherein said adhesive surface comprises a pressure-sensitive absorbent adhesive, said intermediate layer comprising a tacky hydrogel or hydrocolloid adhesive, said tacky hydrogel or hydrocolloid adhesive characterized as having a greater absorbent capacity than does the hydrogel of said hydrogel layer underlying said intermediate layer; said underlying hydrogel layer is characterized as being more wound friendly and consequently more suitable for direct wound contact than the tacky hydrogel or hydrocolloid adhesive of greater absorbent capacity; said intermediate layer having sufficient moisture permeability to permit at least a portion of wound exudate to diffuse therethrough to the outer surface of said dressing; and
(c) an outer oxygen- and vapor-permeable layer adapted for transpiration of at least a portion of fluid diffusing through said dressing.

8. A dressing as defined in claim 7 wherein said absorbent adhesive comprises said tacky hydrogel, said tacky hydrogel being a polymer of 2-acrylamido-2-methylpropane sulfonic acid or a salt thereof.

9. A wound dressing as defined in claim 8 wherein said hydrogel layer is substantially thicker than said intermediate layer.

10. A wound dressing as defined in claim 8 wherein said outer layer is characterized as having a low friction sliding surface which materially inhibits accidental movement of said dressing and consequent disturbance of the wound.

* * * * *

REEXAMINATION CERTIFICATE (2328th)
United States Patent [19]
Quarfoot et al.

[11] B1 4,909,244
[45] Certificate Issued Jul. 5, 1994

[54] HYDROGEL WOUND DRESSING

[75] Inventors: Alan J. Quarfoot, Palatine; Patrick H. Hyla, Lake Zurich; Donald Patience, Barrington, all of Ill.

[73] Assignee: The Kendall Company, Boston, Mass.

Reexamination Request:
No. 90/003,049, May 7, 1993

Reexamination Certificate for:
Patent No.: 4,909,244
Issued: Mar. 20, 1990
Appl. No.: 935,426
Filed: Nov. 26, 1986

[51] Int. Cl.⁵ .............................................. A61L 15/00
[52] U.S. Cl. .................... 602/48; 424/78.06; 428/319.3; 428/423.4; 604/304

[56] References Cited
U.S. PATENT DOCUMENTS 3,972,328  8/1976  Chen.
4,466,953  8/1984  Keith et al.
4,538,603  9/1985  Pawelchak et al.
4,631,227  12/1986  Nakamura.

*Primary Examiner*—Randall L. Green

[57] ABSTRACT

A wound dressing adapted for preventing pooling of wound exudate and for promoting healing comprises, in order:

(a) a layer consisting essentially of hydrogel for placement on a wound, the hydrogel being characterized as being wound friendly and for absorbing and acting as a reservoir for wound exudate;

(b) an intermediate layer disposed over said hydrogel layer. The intermediate layer comprises a tacky hydrogel or hydrocolloid adhesive, the tacky hydrogel or hydrocolloid adhesive characterized as having a greater absorbent capacity that does the hydrogel in the hydrogel layer; the underlying hydrogel layer is characterized as being more friendly and consequently more suitable for direct wound contact than the overlying adhesive hydrogel of greater absorbent capacity; the intermediate layer having sufficient moisture permeability therethrough to the surface of the dressing;

(c) an outer oxygen- and vapor-permeable layer adapted for transpiration of at least a portion of fluid diffusing through the dressing.

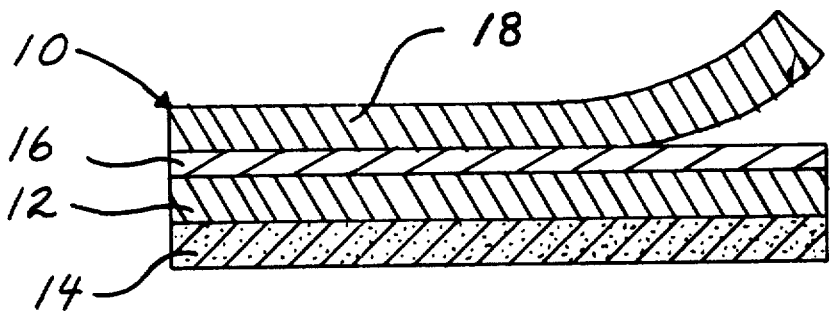

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 to 10 is confirmed.

* * * * *